United States Patent [19]
Boelle et al.

[11] Patent Number: 5,698,595
[45] Date of Patent: Dec. 16, 1997

[54] USE OF SULFONIC ACIDS AS ANTI-AGEING AGENTS IN A COSMETIC OR DERMATOLOGICAL COMPOSITION

[75] Inventors: Jean Paul Boelle, Meudon; Jean-Pierre Laugier, Antony; Serge Forestier, Claye Souilly, all of France

[73] Assignee: L'Oreal, Paris, France

[21] Appl. No.: 770,061

[22] Filed: Dec. 19, 1996

Related U.S. Application Data

[63] Continuation of Ser. No. 401,140, Mar. 8, 1995, abandoned.

[30] Foreign Application Priority Data

Mar. 8, 1994 [FR] France ................... 94 02657

[51] Int. Cl.$^6$ ............ A61K 31/185; A61K 31/125; A61K 2/44
[52] U.S. Cl. ............ 514/576; 424/59; 424/60; 514/577; 514/692; 562/100; 568/326
[58] Field of Search ............ 424/60; 514/692, 514/576, 577; 568/326; 562/100

[56] References Cited

U.S. PATENT DOCUMENTS

| | | | |
|---|---|---|---|
| 5,144,084 | 9/1992 | Heywang et al. | 568/326 |
| 5,302,376 | 4/1994 | Forestier et al. | 424/59 |

FOREIGN PATENT DOCUMENTS

| | | |
|---|---|---|
| A-0457687 | 11/1991 | European Pat. Off. |
| A-0531192 | 3/1993 | European Pat. Off. |
| A-2645148 | 10/1990 | France . |
| A-2185019 | 7/1987 | United Kingdom . |

*Primary Examiner*—Shelley A. Dodson
*Attorney, Agent, or Firm*—Oblon, Spivak, McClelland, Maier & Neustadt, P.C.

[57] ABSTRACT

Application of a compound having at least one sulfonic acid functional group which is at least partially non-neutralized, in a cosmetic or dermatological composition, to the skin is useful for treating intrinsic ageing of the skin.

28 Claims, No Drawings

USE OF SULFONIC ACIDS AS ANTI-AGEING AGENTS IN A COSMETIC OR DERMATOLOGICAL COMPOSITION

This is a continuation of application Ser. No. 08/401,140, filed on Mar. 8, 1995, now abandoned.

BACKGROUND OF THE INVENTION

1. Field of the Invention

The present invention relates to novel cosmetic and/or dermatological compositions useful for combating the intrinsic ageing of the skin and a method for combating the intrinsic ageing of skin by applying such a composition to the skin.

2. Discussion of the Background

The signs of ageing of the skin resulting from the effects on the skin of intrinsic or extrinsic factors are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telangiectasia.

Some of these signs are more particularly associated with intrinsic or physiological ageing, that is to say with "normal" ageing associated with age, whereas others are more specific to extrinsic ageing, that is to say of ageing caused by the environment in general; such ageing is more particularly photo-ageing due to exposure to the sun, to light or to any other radiation.

The changes in the skin which occur due to intrinsic ageing are the consequence of a genetically programmed sequence involving endogenous factors. This intrinsic ageing in particular causes a slowing down of the regeneration of skin cells, which is reflected essentially in the appearance of clinical damage such as a reduction of the subcutaneous adipose tissue and the appearance of fine lines or small wrinkles, and in histopathological changes such as an increase in the number and thickness of the elastic fibers, a loss of vertical fibers from the elastic tissue membrane and the presence of large irregular fibroblasts in the cells of this elastic tissue.

In contrast, extrinsic ageing results in clinical damage such as thick wrinkles and the formation of flabby and weather-beaten skin, and in histopathological changes such as an excessive accumulation of elastic substance in the upper dermis and degeneration of the collagen fibers.

Various cosmetic compositions intended to combat ageing of the skin are known in the prior art. Retinoic acid and derivatives thereof have been described as anti-ageing agents in cosmetic compositions, in particular in U.S. Pat. No. 4,603,146.

α-Hydroxy acids such as lactic acid, glycolic or alternatively citric acid are also known for this same application, these acids having been described in numerous patents and publications (see for example European Patent Application EP-A-413 528) and introduced into numerous cosmetic compositions on the market.

Aromatic ortho-hydroxy acids such as salicylic acid have also been proposed (see for example PCT Patent Applications WO 93/10756 and WO 93/10755).

All of these compounds act against ageing of the skin by desquamation, that is to say removal of the dead cells at the surface of the stratum corneum. This desquamation is also referred to as a keratolytic property. However, these compounds also have side effects, consisting of stinging and redness which the user finds unpleasant.

Thus, there remains a need for anti-ageing agents which are at least as effective as the compounds of the prior art, but do not exhibit their drawbacks, and in particular for agents effective against instrinsic ageing. There also remains a need for a method of combating intrinsic ageing which is at least as effective as the prior method but does not suffer from their drawbacks.

SUMMARY OF THE INVENTION

Accordingly, it is one object of the present invention to provide novel compositions for combating the intrinsic ageing of the skin.

It is another object of the present invention to provide novel compositions for combating the intrinsic ageing of the skin, which exhibit a reduced tendency to cause burning or stinging of the skin.

It is another object of the present invention to provide novel methods for combating the intrinsic ageing of the skin.

It is another object of the present invention to provide novel methods for combating the intrinsic ageing of the skin, which exhibit a reduced tendency to cause burning or stinging of the skin.

These and other objects, which will become apparent during the following detailed description, have been achieved by the inventors' discovery that compounds having at least one sulfonic acid function which is at least partially non-neutralized may be used in a cosmetic composition as agents acting against the intrinsic or physiological ageing of the skin.

The inventors have observed, without a full explanation for this being available, that these compounds exhibit an anti-ageing action which is at least as effective as the compounds of the prior art which are all carboxylic acids, and that this action is milder insofar as no irritation is experienced and no redness is observed when a cosmetic or dermatological composition containing them is applied to the skin.

Some of these sulfonic acids have been used previously in anti-sun compositions for protecting the skin against ultraviolet radiation, that is to say for protecting the skin against the erythema and burns caused by light radiation of wavelengths between 280 and 400 nm, and more particularly between 280 and 360 nm. Such compositions are described in particular in the following documents: U.S. Pat. No. 4,585,597, and French Patent Nos. 2,236,515, 2,282,426, 2,645,148, 2,430,938 and 2,592,380. The protection against the sun enables the skin to be protected against photoageing, but it does not treat intrinsic ageing. In addition, none of these documents suggests the treatment of physiological ageing by these sulfonic acids.

These sulfonic acids are used generally in their totally neutralized form, this form being unsuitable for treatment of the intrinsic ageing of the skin.

One embodiment of the present invention is thus compositions which contain at least one compound having at least one sulfonic acid function which is at least partially nonneutralized which are useful for combating intrinsic ageing of the skin.

Another embodiment of the present invention is a method for combating the intrinsic ageing of the skin by applying to the skin at least one compound having at least one sulfonic acid function which is at least partially non-neutralized in a cosmetic and/or dermatological composition.

An additional embodiment of the present invention is a method for combating wrinkles and/or fine lines due to intrinsic ageing by applying to the skin at least one compound having at least one sulfonic acid function which is at least partially non-neutralized in a cosmetic and/or dermatological composition.

A further embodiment of the present invention is a method for removing dead cells from the skin by applying to the skin at least one compound having at least one sulfonic acid function which is at least partially non-neutralized in a cosmetic and/or dermatological composition.

The present invention has a very specific additional advantage when the sulfonic acids which are used as sunscreen agents in the prior art are used in their partially non-neutralized form. Indeed, in this case, the skin is also protected from the harmful effects of ultraviolet radiation by virtue of the capacity of these specific sulfonic acids, even in their acid form, to filter solar radiation.

DETAILED DESCRIPTION OF THE PREFERRED EMBODIMENTS

The sulfonic acids which may be used in the context of the present invention may be represented by the general formula (a):

R—SO$_3$H  (a)

in which R represents an optionally substituted aliphatic or aromatic hydrocarbon residue.

According to a specific embodiment of the invention, R is chosen from the group comprising alkyl radicals having from about 1 to about 30 carbon atoms and alkenyl radicals having from about 2 to about 30 carbon atoms, these radicals being linear or branched and optionally substituted with one or more hydroxyl, $C_{1-4}$-alkoxy, $C_{2-18}$-alkanoyloxy, formyl, $C_{6-10}$-aryl, $C_{3-6}$-cycloalkyl or $C_{7-25}$-polycycloalkyl groups.

Examples of such compounds which may be mentioned are: methanesulfonic acid, CH$_3$SO$_3$H; ethanesulfonic acid, CH$_3$CH$_2$SO$_3$H; n-butane-1-sulfonic acid, CH$_3$CH$_2$CH$_2$CH$_2$SO$_3$H; n-dodecane-1-sulfonic acid, CH$_3$—(CH$_2$)$_{11}$—SO$_3$H; n-octadecane-1-sulfonic acid, CH$_3$—(CH$_2$)$_{17}$—SO$_3$H; vinylsulfonic acid, CH$_2$=CHSO$_3$H; 2-hydroxyethane-1-sulfonic acid, HO—CH$_2$CH$_2$SO$_3$H; 4-hydrobutane-1-sulfonic acid, HO—(CH$_2$)$_4$SO$_3$H; and 10-camphorsulfonic acid.

According to another specific embodiment of the invention, R is an aryl residue having from 6 to 10 carbon atoms, which is optionally substituted with one or more hydroxyl, $C_{1-4}$-alkoxy, $C_{2-4}$-alkenyloxy, $C_{1-4}$-alkyl, $C_{2-4}$-alkanoyloxy, $C_{6-10}$-aryl, $C_{6-10}$-aryloxy, $C_{6-10}$-aroyl, $C_{6-10}$-aroyloxy, carboxyl, halo or sulfonyl groups.

Examples of such compounds which may be mentioned are: benzenesulfonic acid:

4-methylbenzenesulfonic acid:

dodecylbenzenesulfonic acid (mixture of isomers):

5-sulfosalicylic acid:

5-sulfoisophthalic acid:

4-methoxybenzenesulfonic acid:

xylenesulfonic acid (mixture of isomers):

3,6-dihydroxynaphthalene-2,7-disulfonic acid:

1,8-dihydroxynaphthalene-3,6-disulfonic acid:

4-chlorobenzenesulfonic acid:

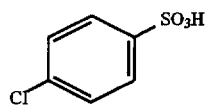

According to another specific embodiment of the invention, sulfonic derivatives having the additional property of filtering UV radiation are used.

Examples of such compounds which may be mentioned are those having the general formula (b) below:

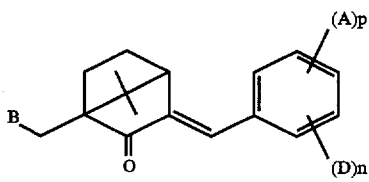

in which

B represents H or SO$_3$H $0 \leq p \leq 1$ with B=SO$_3$H when p=0

$0 \leq n \leq 4$

D represents one or more linear or branched alkyl or alkenyl or alkenyloxy or alkoxy radicals or halo or hydroxy radicals which may be identical or different when n≧2, the alkyl, alkenyl, alkenyloxy or alkoxy radicals containing from about 1 to about 18 carbon atoms, A, preferably in the meta or para position, represents either an SO$_3$H radical;

or a group:

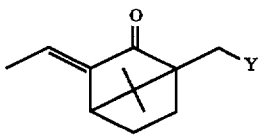

in which Y represents H or SO$_3$H or a group:

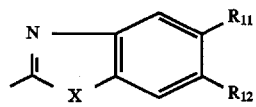

in which:

R$_{11}$ denotes a hydrogen atom, a linear or branched alkyl or alkoxy radical containing from about 1 to about 6 carbon atoms or the SO$_3$H radical, R$_{11}$ being SO$_3$H when B=H, R$_{12}$ denotes a hydrogen atom, or a linear or branched alkyl or alkoxy radical containing from about 1 to about 6 carbon atoms, and X is an oxygen or sulphur atom or a group —NR—, R being a hydrogen atom or a linear or branched alkyl radical containing from about 1 to about 6 carbon atoms.

Specific examples of compounds of formula (b) which may be mentioned are the following derivatives of formulae (I), (II) and (III):

Formula (I):

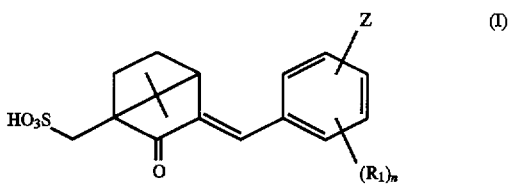

in which:

Z, preferably in the para or meta position, denotes a group:

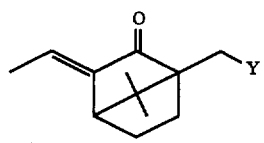

in which Y represents H or SO$_3$H n is equal to 0 or is an integer between 1 and 4 ($0 \leq n \leq 4$)

R$_1$ represents one or more linear or branched alkyl or alkoxy radicals, which may be identical or different, containing from about 1 to about 4 carbon atoms.

A particularly preferred compound of formula I is that corresponding to n=0, Z in the para position and Y=SO$_3$H: benzene-1,4-[di(3-methylidene-10-camphorsulfonic)] acid.

Formula (II):

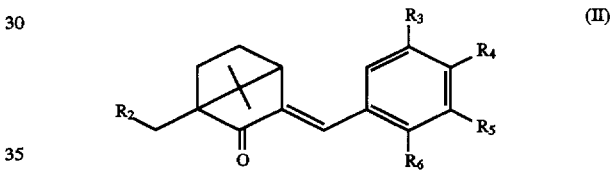

in which:

R$_2$ denotes a hydrogen atom or an —SO$_3$H radical,

R$_3$, R$_4$, R$_5$ and R$_6$, which may be identical or different, represent a hydroxyl group, a linear or branched alkyl radical having from about 1 to about 4 carbon atoms, a linear or branched alkenyl radical having from about 2 to about 4 carbon atoms, a linear or branched alkoxy radical having from about 1 to about 4 carbon atoms, a linear or branched alkenyloxy radical having from 2 to 4 carbon atoms, or a halo radical; in addition, only one radical R$_3$ to R$_6$ may be an SO$_3$H radical, at least one of the radicals R$_3$ to R$_6$ denoting the —SO$_3$H radical when R$_2$ is a hydrogen atom.

Specific examples which may be mentioned are the following compounds of formula II in which:

R$_4$ denotes the —SO$_3$H radical in the para position of benzylidenecamphor R$_2$, R$_3$, R$_5$ and R$_6$ each denote a hydrogen atom, that is to say 3-benzylidenecamphor-4'-sulfonic acid.

R$_3$, R$_4$, R$_5$ and R$_6$ each denote a hydrogen atom and R$_2$ denotes an SO$_3$H radical, that is to say 3-benzylidene-10-camphorsulfonic acid.

R$_4$ denotes a methyl radical in the para position of the benzylidenecamphor, R$_5$ denotes an —SO$_3$H radical and R$_2$, R$_3$ and R$_6$ represent a hydrogen atom, that is to say 3-benzylidenecamphor-4'-methyl-3'-sulfonic acid.

R$_4$ denotes a chlorine atom in the para position of the benzylidenecamphor, R$_5$ denotes an —SO$_3$H radical and R$_2$, R$_3$ and R$_6$ represent a hydrogen atom, that is to say 3-benzylidenecamphor-4'-chloro-3'-sulfonic acid.

R$_4$ denotes a methyl radical in the para position of the benzylidenecamphor, R$_3$, R$_5$ and R$_6$ denote a hydrogen atom and $R_2$ denotes an —$SO_3H$ radical, that is to say 4'-methyl-3-benzylidene-10-camphorsulfonic acid.

$R_2$ denotes an $SO_3H$ radical, $R_3$ is a methyl radical, $R_4$ is a hydrogen atom, $R_5$ is a tert-butyl radical and $R_6$ is a hydroxyl radical, that is to say 3-(3-t-butyl-2-hydroxy-5-methyl)benzylidene-10-camphorsulfonic acid.

$R_2$ represents an $SO_3H$ radical, $R_3$ is a methoxy radical, $R_4$ is a hydrogen atom, $R_5$ is a tert-butyl radical and $R_6$ is a hydroxyl radical, that is to say 3-(3-t-butyl-2-hydroxy-5-methoxy)benzylidene-10-camphorsulfonic acid.

$R_2$ represents an $SO_3H$ radical, $R_3$ and $R_5$ each denote a tert-butyl radical, $R_4$ denotes a hydroxyl radical and $R_6$ denotes a hydrogen atom, that is to say 3-(3,5-di-ter-butyl-4-hydroxy)benzylidene-10-camphorsulfonic acid.

$R_4$ represents a para-methoxy radical, $R_5$ represents $SO_3H$, and the radicals $R_2$, $R_3$ and $R_6$ represent H, that is to say 3-benzylidenecamphor-4'-methoxy-3'-sulfonic acid.

$R_2$ denotes an —$SO_3H$ radical, $R_3$ and $R_6$ represent H, and $R_4$ and $R_5$ form a methylenedioxy radical, that is to say 3-(4,5-methylenedioxy)benzylidene-10-camphorsulfonic acid.

$R_2$ represents an —$SO_3H$ radical, $R_4$ represents a methoxy radical and the radicals $R_3$, $R_5$ and $R_6$ represent H, that is to say 3-(4-methoxy)benzylidene-10-camphorsulfonic acid.

$R_2$ represents an —$SO_3H$ radical, $R_4$ and $R_5$ are both a methoxy radical and the radicals $R_3$ and $R_6$ represent H, that is to say 3-(4,5-dimethoxy)benzylidene-10-camphorsulfonic acid.

$R_2$ represents an —$SO_3H$ radical, $R_4$ is an n-butoxy radical and the radicals $R_3$, $R_5$ and $R_6$ represent a hydrogen atom, that is to say 3-(4-n-butoxy)benzylidene-10-camphorsulfonic acid.

$R_2$ represents an —$SO_3H$ radical, $R_4$ is an n-butoxy radical, $R_5$ is a methoxy radical and $R_3$ and $R_6$ both denote a hydrogen atom, that is to say 3-(4-n-butoxy-5-methoxy) benzylidene-10-camphorsulfonic acid.

Formula (III):

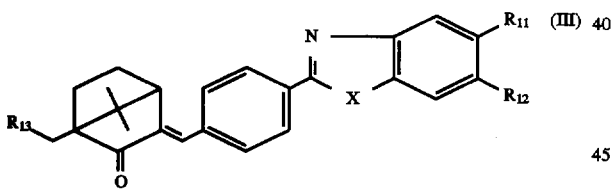

in which:

$R_{11}$ denotes a hydrogen atom, a linear or branched alkyl or alkoxy radical containing from about 1 to about 6 carbon atoms or an —$SO_3H$ radical, $R_{12}$ denotes a hydrogen atom or a linear or branched alkyl or alkoxy radical containing from about 1 to about 6 carbon atoms, $R_{13}$ denotes a hydrogen atom or an —$SO_3H$ radical, at least one of the radicals $R_{11}$ and $R_{13}$ denoting an —$SO_3H$ radical, X is an oxygen or sulphur atom or a group —NR—, R being a hydrogen atom or a linear or branched alkyl radical containing from 1 to 6 carbon atoms approximately.

A specific example of formula (III) which may be mentioned is: the compound in which X denotes an —NH— radical, $R_{11}$ denotes an —$SO_3H$ radical, and $R_{12}$ and $R_{13}$ both denote a hydrogen atom, that is to say 2-[4-(camphomethylidene)phenyl]benzimidazole-5-sulfonic acid.

The compounds of structures (I), (II) and (III) are described in U.S. Pat. No. 4,585,597 and in French Patent Nos. 2,236,515, 2,282,426, 2,645,148, 2,430,938 and 2,592, 380.

Other examples of compounds also having the property of filtering UV radiation which may be mentioned are the compounds of general formula (c) below:

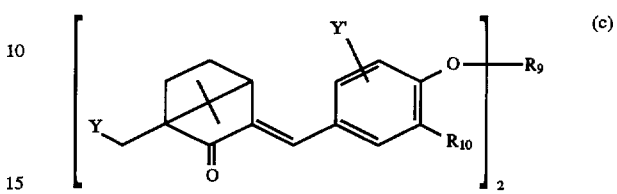

in which:

$R_9$ denotes a divalent radical: —$(CH_2)_m$— or —$CH_2$—CHOH—$CH_2$—, m being an integer between 1 and 10 ($1 \leq m \leq 10$), $R_{10}$ denotes a hydrogen atom or an alkoxy radical containing from about 1 to about 4 carbon atoms, Y and Y' denote a hydrogen atom or an —$SO_3H$ radical, at least one of these radicals Y or Y' is other than hydrogen.

Specific examples which may be mentioned are the following compounds of formula (c) in which Y represents $SO_3H$, Y' is H, $R_{10}$ is H and $R_9$ is —$CH_2$—$CH_2$—, that is to say ethylenebis[3(4'-oxybenzylidene)-10-camphorsulfonic] acid.

Examples of sulfonic derivatives having the additional property of a UV radiation screening agent which may also be mentioned are the compounds of general formula (d) below:

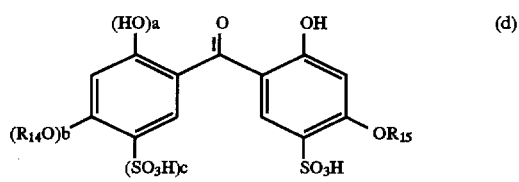

in which:

$R_{14}$ and $R_{15}$, which may be identical or different, denote either a hydrogen atom or a linear or branched alkyl radical containing from about 1 to about 8 carbon atoms, a, b and c, which may be identical or different, are equal to 0 or 1.

A specific example of a compound of formula (d) which may be mentioned is: 2-hydroxy-4-methoxybenzophenone-5-sulfonic acid (compound of formula (d) in which a, b and c are equal to zero, and $R_{15}$ denotes a methyl radical), this compound being denoted in the CTFA dictionary as benzophenone-4.

Another example of sulfonic derivatives also having the property of filtering UV radiation has the general formula (e):

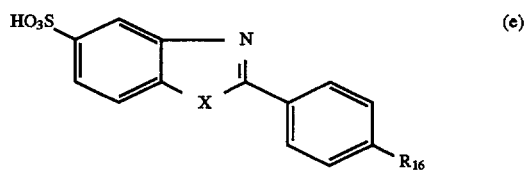

in which:

X denotes an oxygen atom or an —NH— radical.

R$_{16}$ denotes a hydrogen atom, a linear or branched alkyl or alkoxy radical containing from about 1 to about 8 carbon atoms or a group of formula

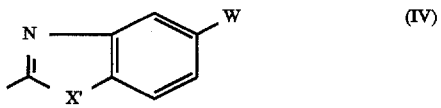

(IV)

in which X' represents an oxygen atom or an —NH— radical and W represents H or SO$_3$H.

Specific examples which may be mentioned are the following compounds of formula (e) in which:

X denotes the —NH— radical and R$_{16}$ denotes a hydrogen atom: 2-phenylbenzimidazole-5-sulfonic acid, which is denoted as "2-phenylbenzimidazole 5-sulfonic 15 acid" in the CTFA dictionary.

X denotes the —NH— radical, R$_{16}$ denotes the group of formula (IV) in which W represents SO$_3$H and X' denotes the —NH— radical: benzene-1,4-di(benzimidazol-2-yl-5-sulfonic) acid.

X denotes an oxygen atom, R$_{16}$ denotes the group of formula (IV) in which W represents SO$_3$H and X' denotes an oxygen atom: benzene-1,4-di(benzoxazol-2-yl-5-sulfonic) acid.

The compounds of formulae (d) and (e) are known compounds which may be prepared according to standard methods described in the prior art.

The sulfonic acids are present in the compositions according to the present invention, in an amount which is preferably between 0.1 and 10% by weight and even more preferably between 0.1 and 5% by weight, based on the total weight of the composition.

The degree of neutralization should not be total. The lower this degree is, the greater will be the actual anti-ageing action of the composition. Suitably, the sulfonic acid in the present composition is neutralized to a degree such that 0 to 90 mole %, preferably 0 to 60 mole %, of the sulfonic acid groups in the composition have been neutralized. This may be achieved by adjusting the pH of the composition to a value of 1 to 6, preferably 3 to 5.

The neutralization is achieved in a conventional manner using an inorganic or organic base such as, for example, sodium hydroxide, potassium hydroxide, aqueous ammonia, monoethanolamine, triethanolamine, isopropanolamine, etc.

The cosmetic compositions according to the invention may contain one or more additional hydrophilic or lipophilic UVA- and/or UVB-active sunscreen agents other than, of course, the acidic hydrophilic agents used in the present invention.

These additional screening agents are preferably chosen from cinnamic derivatives such as, for example, 2-ethylhexyl p-methoxycinnamate, salicylic derivatives such as, for example, 2-ethylhexyl salicylate and homomenthyl salicylate, camphor derivatives such as, for example, 3-(4-methylbenzylidene)camphor, triazine derivatives such as 2,4,6-tris[p-(2'-ethylhexyl-1'-oxycarbonyl)anilinol]1,3,5-triazine, benzophenone derivatives such as 2-hydroxy-4-methoxybenzophenone, dibenzoylmethane derivatives such as 4-tert-butyl-4'-methoxydibenzoylmethane, β,β-diphenylacrylate derivatives such as 2-ethylhexyl α-cyano-β,β-diphenylacrylate, (octyl 2-cyano-3,3-diphenyl-2-propenoate), p-aminobenzoic acid derivatives such as, for example, octyl para-dimethylaminobenzoate, menthyl anthranilate, screening polymers and screening silicones described in PCT Patent Application WO-93-04665.

As additional screening agents, it is also possible to use inorganic substances such as nanopigments of a metal oxide, titanium oxide, iron oxide, zinc oxide and zirconium oxide in particular.

The compositions of the invention may also comprise the cosmetic adjuvants conventionally used, such as fats, organic solvents, ionic or nonionic thickening agents, emollients, antioxidants, opacifying agents, stabilizers, silicones, anti-foaming agents, moisturizing agents, vitamins, fragrances, preserving agents, ionic or nonionic surfactants, fillers, sequestering agents, dyes or any other ingredient usually used in cosmetics.

The compositions according to the invention are prepared according to the techniques which are well known to those skilled in the art in the field.

The compositions according to the invention may be provided in the form of a suspension or a dispersion in solvents or in fats, in the form of a vesicle dispersion or alternatively in the form of an emulsion such as a cream or a milk, in the form of an ointment, a gel, a solid stick, an aerosol foam or a spray.

The present method of combating the intrinsic ageing of the skin is carried out by applying the present composition to the skin. Suitably, the present composition is applied to the skin in an amount such that 0.002 to 0.2 mg/cm$^2$, preferably 0.002 to 0.1 mg/cm$^2$, of the partially non-neutralized sulfonic acid compound is applied to the skin. The present composition may be applied one or more times daily or less frequently. In a preferred embodiment, the composition is applied to the skin within one or two hours prior to exposure of the skin to intense radiation, such as sunbathing.

Other features of the invention will become apparent in the course of the following descriptions of exemplary embodiments which are given for illustration of the invention and are not intended to be limiting thereof.

EXAMPLES

In the following examples the percentages are given by weight. The term "qs 100%" means that a sufficient amount of that ingredient was present to make the sum of the amounts for all ingredients equal 100%.

Example 1

A care cream having the following composition is prepared:

| | |
|---|---|
| Span 65 ® (ICI) | 1% |
| Glyceryl monostearate | 3% |
| Myrj 52 ® (ICI) | 2% |
| Ketostearyl alcohol (50—50) | 4% |
| Perhydrosqualene | 15% |
| Liquid petrolatum | 2% |
| Glycerol | 3% |
| Sepigel 305 ® (SEPPIC) | 1% |
| Disodium EDTA | 0.05% |
| Preserving agents | 0.1% |
| Benzene-1,4-[di(3-methylidene-10-camphorsulfonic)] acid | 0.7% |
| Demineralized water | qs 100% |
| pH of the formula: 2 | |

Example 2

A care cream having the following composition is prepared:

| | |
|---|---|
| Span 65 ® (ICI) | 1% |
| Glyceryl monostearate | 3% |

-continued

| | |
|---|---|
| Myrj 52 ® (ICI) | 2% |
| Ketostearyl alcohol (50—50) | 4% |
| Perhydrosqualene | 15% |
| Liquid petrolatum | 2% |
| Glycerol | 3% |
| Sepigel 305 ® (SEPPIC) | 1% |
| Disodium EDTA | 0.05% |
| Preserving agents | 0.1% |
| Benzene-1,4-[di(3-methylidene-10-camphorsulfonic)] acid | 0.7% |
| Demineralized water | qs 100% |
| Triethanolamine | 0.4% |
| pH of the formula: 4 | |

Example 3

A gel having the following composition is prepared:

| | |
|---|---|
| Carbomer 934 P ® (GOODRICH) | 1% |
| Glycerol | 3% |
| Propylene glycol | 3% |
| Xanthan gum | 0.4% |
| Eusolex 232 ® (MERCK) | 1% |
| Triethanolamine | 0.1% |
| Demineralized water | qs 100% |
| pH of the formula: 4 | |

Example 4

A serum having the following composition is prepared:

| | |
|---|---|
| Miglyol 812 ® (DYNAMIT NOBEL) | 0.5% |
| Disodium EDTA | 0.05% |
| Fragrance/preserving agents | 0.5% |
| Carbomer 940 ® (GOODRICH) | 0.3% |
| Xanthan gum | 0.15% |
| Glycerol | 3% |
| Cetyl alcohol | 0.1% |
| Copra diethanolamine | 0.1% |
| Glyceryl monostearate | 0.3% |
| PEG 100 stearate | 0.3% |
| Benzene-1,4-[di(3-methylidene-10-camphorsulfonic)] acid | 1% |
| Demineralized water | qs 100% |
| pH of the formula: 3.8 | |

Example 5

A cream having the following composition is prepared:

| | |
|---|---|
| Myrj 52 ® (I.C.I.) | 2% |
| Span 65 ® (I.C.I.) | 1% |
| Glyceryl monostearate | 2.5% |
| Liquid petrolatum | 2% |
| Cyclomethicone | 15% |
| Propylene glycol | 3% |
| Glycerol | 3% |
| Cetyl alcohol | 3% |
| Camphor-10-sulfonic acid | 1% |
| Triethanolamine | 0.3% |
| Demineralized water | qs 100% |

Example 6

A cream having the following composition is prepared:

| | |
|---|---|
| Myrj 52 ® (I.C.I.) | 1.5% |
| Span 65 ® (I.C.I.) | 1% |
| Glyceryl monostearate | 2.5% |
| Liquid petrolatum | 3% |
| Parsol MCX ® (Givaudan) | 0.5% |
| Apricot kernel oil | 13% |
| Propylene glycol | 3% |
| Glycerol | 3% |
| Ketostearyl alcohol | 3% |
| UVINUL MS 40 ® (B.A.S.F.) | 1% |
| Demineralized water | qs 100% |

Example 7

A cream having the following composition is prepared:

| | |
|---|---|
| Myrj 52 ® (I.C.I.) | 2% |
| Span 65 ® (I.C.I.) | 1% |
| Glyceryl monostearate | 3% |
| Cetyl alcohol | 2% |
| Liquid petrolatum | 17% |
| Glycerol | 3% |
| Sepigel 305 ® (SEPPIC) | 1% |
| Disodium EDTA | 0.05% |
| Ethanesulfonic acid | 0.5% |
| Triethanolamine | 0.1% |
| Demineralized water | qs 100% |

Example 8

A fluid having the following composition is prepared:

| | |
|---|---|
| Hydrogenated soya lecithin | 0.5% |
| Generol 122 E5 ® (HENKEL) | 0.2% |
| Apricot kernel oil | 2.5% |
| Disodium EDTA | 0.05% |
| SEPIGEL 305 ® (SEPPIC) | 0.15% |
| CARBOPOL 980 ® (GOODRICH) | 0.4% |
| Glycerol | 6% |
| Demineralized water | qs 100% |
| EUSOLEX 232 ® (MERCK) | 0.5% |
| Benzene-1,4-[di(methylidene-10-camphorsulfonic)] acid | 0.5% |
| Triethanolamine | 0.2% |

Example 9

A care cream having the following composition is prepared:

| | |
|---|---|
| Myrj 52 ® (I.C.I.) | 2% |
| Span 65 ® (I.C.I.) | 1% |
| Glyceryl monostearate | 2% |
| PARSOL MCX ® (MERCK) | 1% |
| Benzene-1,4-[di(methylidene-10 camphorsulfonic)] acid | 0.7% |
| Propylene glycol | 3% |
| Glycerol | 3% |
| Cetyl alcohol | 3% |
| Demineralized water | qs 100% |
| Sunflower oil | 18% |
| Triethanolamine | 0.1% |

Example 10

A tonic lotion having the following composition is prepared:

| | |
|---|---|
| Benzene-1,4-[di(methylidene-10-camphorsulfonic)] acid | 0.5% |
| UVINUL MS 40 ® (BASF) | 0.5% |
| Methyl para-oxybenzoate | 0.1% |
| Triethanolamine | 0.1% |
| Disodium EDTA | 0.05% |
| PEMULEN TR1 ® (GOODRICH) | 0.15% |
| Glycerol | 3% |
| Propylene glycol | 2% |
| D Panthenol | 0.2% |
| Demineralized water | qs 100% |

Example 11

A care cream having the following composition is prepared:

| | |
|---|---|
| Liquid petrolatum | 15.0% |
| Demsconet 390 ® (Tensia) | 7.0% |
| Géléol Copeaux ® (Gattefossé) | 2.0% |
| Lorol C16 ® (Henkel) | 1.5% |
| Silbione 70 047 V 300 ® (Rhône-Poulenc) | 1.5% |
| Benzene-1,4-[di(methylidene-10-camphorsulfonic)] acid | 2.0% |
| Parsol MCX ® (Givaudan Roure) | 5.0% |
| Butylparaben | 0.2% |
| Germal 115 | 0.2% |
| Water | qs 100% |
| pH of the formula: 1.3 | |

Example 12: Comparative Example

The composition described in Example 1 was the subject of a clinical study in the treatment of physiological ageing of the skin, in comparison with a reference product having the following composition: Salicylic acid 1% Excipient qs 100% marketed under the brand name TURNAROUND®.

A blind testing was carried out on 30 jurors who used the above products comparatively for 5 days: each of the products was applied in an equal amount to half of the face.

On the criteria of the signs of physiological ageing of the skin, both products have an action which is not significantly different.

From the point of view of comfort and tolerance, only 1 juror out of 30 stopped the test with the formula of Example 1 whereas with the reference cream, 7 jurors stopped the test.

The formulae which are the subject of the present invention thus have a proven effectiveness in the treatment of physiological ageing of the skin without displaying the drawbacks of the preparations of the prior art.

This application is based on French Patent Application 94-02657, filed on Mar. 8, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for combating intrinsic aging of the skin, comprising applying to the skin a composition which comprises at least one compound which contains at least one sulfonic acid functional group which is at least partially non-neutralized, said composition having a pH of from 1 to 4.

2. A method of claim 1, wherein said compound has the general formula $$RSO_3H \quad \text{(a)}$$

wherein R is an optionally substituted aliphatic or aromatic hydrocarbon radical.

3. The method of claim 2, wherein R is an aliphatic hydrocarbon residue selected from the group consisting of linear or branched alkyl radicals having from 1 to 30 carbon atoms which may be substituted with one or more hydroxyl, $C_{1-4}$-alkoxy, $C_{2-18}$-alkanoyloxy, formyl, $C_{6-10}$-aryl, $C_{3-6}$-cycloalkyl, or $C_{7-25}$-polycycloalkyl groups, and linear or branched alkenyl radicals having from 2 to 30 carbon atoms, which may be substituted with one or more hydroxyl, $C_{1-4}$-alkoxy, $C_{2-18}$-alkanoyl, formyl, $C_{6-10}$-aryl, $C_{3-6}$-cycloalkyl or $C_{7-25}$-polycycloalkyl groups.

4. The method of claim 2, wherein R is $CH_3$ or $CH_3$—$(CH_2)_{11}$.

5. The method of claim 2, wherein said compound is camphor-10-sulfonic acid.

6. The method of claim 2, wherein R is an aromatic hydrocarbon residue having from 6 to 10 carbon atoms, which may be substituted with one or more hydroxyl, $C_{1-4}$-alkoxy, $C_{2-4}$-alkenyloxy, $C_{1-4}$-alkyl, $C_{2-4}$-alkanoyloxy, $C_{6-10}$-aryl, $C_{6-10}$-aryloxy, $C_{6-10}$-aroyl, $C_{6-10}$-aroyloxy, carboxyl, halo or sulfonyl groups.

7. The method of claim 2, wherein R is $C_6H_5$.

8. The method of claim 5, wherein R is

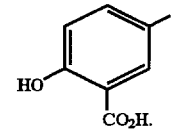

9. The method of claim 2, wherein said compound has the general formula:

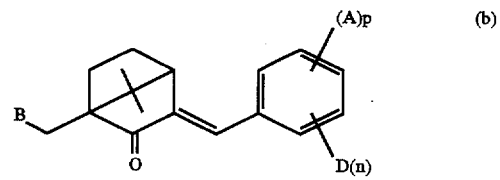

wherein:

B is H or $SO_3H$ $0 \leq p \leq 1$ with B=$SO_3H$ when p=0

$0 \leq n \leq 4$

D is one or more linear or branched alkyl, linear or branched alkenyl, linear or branched alkenyloxy, or linear or branched alkoxy radicals or halo or hydroxy radicals which may be identical or different when $n \geq 2$, said alkyl, alkenyl, alkenyloxy or alkoxy radicals containing from 1 to 18 carbon atoms, A, represents either an $SO_3H$ radical or a group

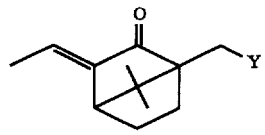

wherein Y is h or SO$_3$H; or a group

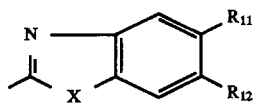

wherein

R$_{11}$ is a hydrogen atom, a linear or branched alkyl group containing from 1 to 6 carbon atoms or a linear or branched alkoxy radical containing from 1 to 6 carbon atoms, the SO$_3$H radical, R$_{11}$ being SO$_3$H when B=H, R$_{12}$ is a hydrogen atom or a linear or branched alkyl group containing 1 to 6 carbon atoms or a linear or branched alkoxy radical containing from 1 to 6 carbon atoms, and X is an oxygen or sulphur atom or a group —NR—, R being a hydrogen atom or a linear or branched alkyl radical containing from 1 to 6 carbon atoms.

10. The method of claim 9, wherein said compound of formula (b) has the formula:

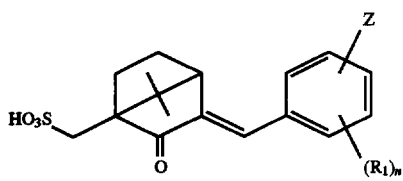

wherein:

Z, is a group

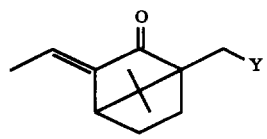

wherein Y is H or SO$_3$H n is equal to 0 or is an integer between 1 and 4 (0≦n≦4)

R$_1$ which may be identical or different, is one or more linear or branched alkyl groups containing 1 to 4 carbon atoms or one or more linear or branched alkoxy radicals, containing 1 to 4 carbon atoms.

11. The method of claim 10, wherein in said compound of formula (I) Z is in the para or meta position.

12. The method of claim 10, wherein said compound of formula (I) is benzene-1,4[di(3-methylidene-10-camphorsulfonic)] acid.

13. The method of claim 9, wherein said compound of formula (b) has the formula:

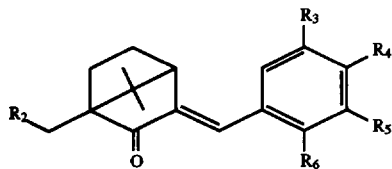

wherein:

R$_2$ is a hydrogen atom or an —SO$_3$H radical,

R$_3$, R$_4$, R$_5$ and R$_6$, which may be identical or different, represent a hydroxyl group, a linear or branched alkyl radical having from 1 to 4 carbon atoms, a linear or branched alkenyl radical having from 2 to 4 carbon atoms, a linear or branched alkoxy radical having from 1 to 4 carbon atoms, a linear or branched alkenyloxy radical having from 2 to 4 carbon atoms, or a halo radical, only one radical R$_3$ to R$_6$ possibly being an SO$_3$H radical, at least one of the radicals R$_3$ to R$_6$ being the —SO$_3$H radical when R$_2$ is a hydrogen atom.

14. The method of claim 13, wherein said compound of formula (II) is selected from the group consisting of 3 benzylidenecamphor-4'-sulfonic acid, 3-benzylidene-10-camphorsulfonic acid, 3-benzylidenecamphor-4'-methyl-3'-sulfonic acid, 3-benzylidenecamphor-4'-chloro-3'-sulfonic acid, 4'-methyl-3-benzylidene-10-camphorsulfonic acid, 3-(3-t-butyl-2-hydroxy-5-methyl)benzylidene-10-camphorsulfonic acid, 3-(3-t-butyl-2-hydroxy-5-methoxy) benzylidene-10-camphorsulfonic acid, 3-(3,5-di-tert-butyl-4-hydroxy)benzylidene-10-camphorsulfonic acid, 3-benzylidenecamphor-4'-methoxy-3'-sulfonic acid, 3-(4,5-methylenedioxy)benzylidene-10-camphorsulfonic acid, 3-(4-methoxy)benzylidene-10-camphorsulfonic acid, 3-(4,5-dimethoxy)benzylidene-10-camphorsulfonic acid, 3-(4-n-butoxy)benzylidene-10-camphorsulfonic acid or 3-(4-n-butoxy-5-methoxy)benzylidene-10-camphorsulfonic acid.

15. The method of claim 9, wherein said compound of formula (b) has the formula:

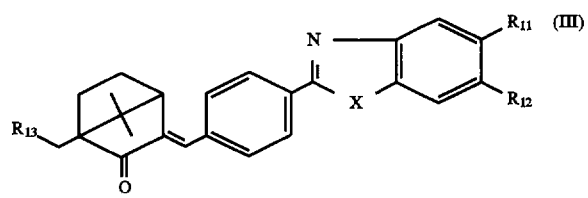

wherein:

R$_{11}$ is a hydrogen atom, a linear or branched alkyl group containing 1 to 6 carbon atoms or a linear or branched alkoxy radical containing 1 to 6 carbon atoms or an —SO$_3$H radical, R$_{12}$ is a hydrogen atom or a linear or branched alkyl group containing 1 to 6 carbon atoms or a linear or branched alkoxy radical containing from 1 to 6 carbon atoms, R$_{13}$ is a hydrogen atom or an —SO$_3$H radical, at least one of the radicals R$_{11}$ and R$_{13}$ is an —SO$_3$H radical, X is an oxygen or sulphur atom or a group —NR—, R being a hydrogen atom or a linear or branched alkyl radical containing from 1 to 6 carbon atoms.

16. The method of claim 15, wherein said compound of formula (III) is 2-[4-(camphomethylidene)phenyl]-benzimidazole-5-sulfonic acid.

17. The method of claim 2, wherein said compound has the formula:

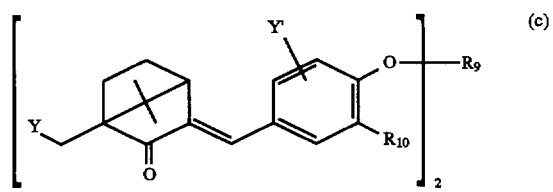

wherein:

R$_9$ is a divalent radical: —(CH$_2$)$_m$— or —CH$_2$—CHOH—CH$_2$, m being an integer between 1 and 10 (1≦m ≦10), R$_{10}$ is a hydrogen atom or an alkoxy radical containing from about 1 to about 4 carbon atoms, Y and Y' are a hydrogen atom or an —SO$_3$H radical, at least one of these radicals Y or Y' is other than hydrogen.

18. The method of claim 17, wherein said compound of formula (c) is ethylenebis[3-(4'-oxybenzylidene)-10-camphorsulfonic acid.

19. The method of claim 2, wherein said compound has the formula:

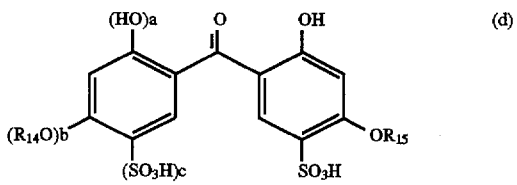

wherein:

$R_{14}$ and $R_{15}$, which may be identical or different, are either a hydrogen atom or a linear or branched alkyl radical containing from 1 to 8 carbon atoms, a, b and c, which may be identical or different, are equal to 0 or 1.

20. The method of claim 9, wherein said compound of formula (d) is 2-hydroxy-4-methoxybenzophenone-5-sulfonic acid.

21. The method of claim 2, wherein said compound has the general formula:

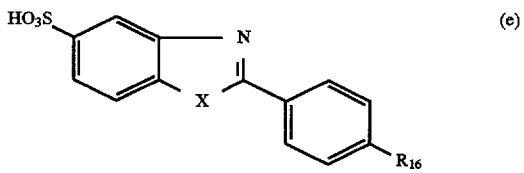

wherein:

X is an oxygen atom or an —NH— radical $R_{16}$ is a hydrogen atom, a linear or branched alkyl group containing 1 to 8 carbon atoms or a linear or branched alkoxy radical containing 1 to 8 carbon atoms or a group of formula

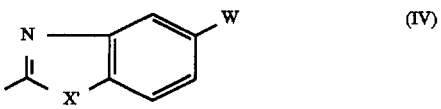

wherein X' is an oxygen atom or an —NH— radical and W is H or $SO_3H$.

22. The method of claim 21, wherein said compound of formula (e) is 2-phenylbenzimidazole-5-sulfonic acid, benzene-1,4-di(benzimidazol-2-yl-5-sulfonic) acid or benzene-1,4-di(benzoxazol-2-yl-5-sulfonic) acid.

23. The method of claim 1, wherein said compound is present in said composition in an amount between 0.1 and 10% by weight, based on the total weight of said composition.

24. The method of claim 2, wherein said compound is present in said composition in an amount between 0.1 and 5% by weight, based on the total weight of said composition.

25. The method of claim 1, wherein 0 to 90% of the sulfonic acid groups in the composition have been neutralized.

26. The method of claim 1, wherein 0 to 60% of the sulfonic acid groups in the composition have been neutralized.

27. The method of claim 1, wherein said composition has a pH of from 3 to 5.

28. The method of claim 9, wherein group A is in the meta or para position.

* * * * *